United States Patent [19]

Cantoni et al.

[11] 4,148,888

[45] Apr. 10, 1979

[54] 3-DEAZAADENOSINE AS AN INHIBITOR OF ADENOSYLHOMOCYSTEINE HYDROLASE WITH ANTIVIRAL ACTIVITY

[75] Inventors: Giulio L. Cantoni, Bethesda; Peter K. Chiang, Kensington, both of Md.; Henry H. Richards, Washington, D.C.

[73] Assignee: The United States of America as represented by the Department of Health, Education and Welfare, Washington, D.C.

[21] Appl. No.: 886,106

[22] Filed: Mar. 13, 1978

[51] Int. Cl.$^2$ .................. A61K 31/70; C12B 9/00; C12L 1/00
[52] U.S. Cl. .................................. 424/180; 195/1.7; 195/1.8; 195/63
[58] Field of Search .................. 424/180; 195/1.7, 1.8, 195/63

[56] References Cited

PUBLICATIONS

Chem. Abst. 9th Coll. Index, vol. 76–85, (1972–1976), p. 19488cs.

Primary Examiner—Sam Rosen
Attorney, Agent, or Firm—John S. Roberts, Jr.

[57] ABSTRACT

3-Deazaadenosine has been found to be an effective antiviral and antifocal agent in tissue culture of animals as evidenced by its activity against Rous sarcoma virus, influenza virus, vesicular stomatitis virus, Sindbis virus, and Newcastle disease virus in the range 0.03–0.3 mM. This compound has also shown use as an inhibitor of adenosylhomocysteine hydrolase from beef liver in the range of 0.001–0.008 mM ($I_{50}$). The antiviral and antifocal effect is correlated with the inhibition of hydrolysis of adenosylhomocysteine in cells. This inhibition of adenosylhomocysteine hydrolase can also be demonstrated in livers of rats injected with 3-deazaadenosine.

7 Claims, No Drawings

3-DEAZAADENOSINE AS AN INHIBITOR OF ADENOSYLHOMOCYSTEINE HYDROLASE WITH ANTIVIRAL ACTIVITY

3-Deazaadenosine is a compound which is a copy of adenosine less the nitrogen at the 3 position. It has been found that this compound, 3-deazaadenosine, inhibits or suppresses the important reversible hydrolysis of S-adenosylhomocysteine according to the following formula:

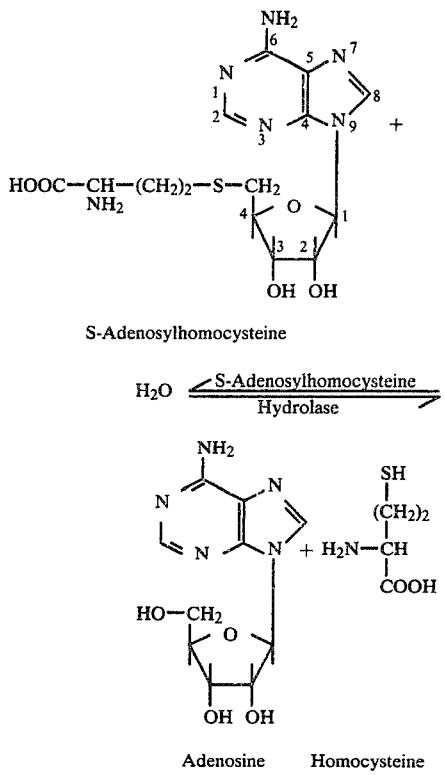

PRIOR ART STATEMENT

The following literature articles point up the background for the utilization of 3-deazaadenosine for suppressing hydrolysis and in an antiviral capacity and these uses are deemed novel.

Peter K. Chiang, Henry H. Richards, and Giulio L. Cantoni, "S-Adenosyl-L-homocysteine Hydrolase: Analogues of S-Adenosyl-L-homocysteine as Potential Inhibitors," Molecular Pharmacology, 13:939–947 (1977).

Peter K. Chiang and Giulio L. Cantoni, "Levels of Adenosylmethionine and Adenosylhomocysteine in Livers of Rats Injected with 3-Deazaadenosine, Methionine and Nicotinamide," [to be published].

Henry H. Richards, Peter K. Chiang and Giulio L. Cantoni, "Adenosylhomocysteine Hydrolase: Crystallization of the Purified Enzyme and Its Properties," [to be published JBC].

It is known that the enzymatic transfer of the methyl group of S-adenosyl-L-methionine yields S-adenosyl-L-homocysteine as one of the products of the reaction. In eukaryotes the principal pathway for the metabolism of adenosylhomocysteine is its hydrolysis to L-homocysteine and adenosine by the action of an enzyme, adenosylhomocysteine hydrolase.

Adenosylhomocysteine (AdoHcy) has been found to inhibit competitively most of the methyltransferases which utilize adenosylmethionine as the methyl donor. Thus, it is further known that the regulation of adenosylhomocysteine hydrolase by various effectors can be of physiological importance in controlling biological methylations.

It has been further found that the present compound, 3-deazaadenosine, may serve as a substrate for the hydrolase enzyme and, by being coupled to L-homocysteine to form 3-deazaadenosylhomocysteine, serves as a factor to shift the reaction noted in the formula above away from the hydrolysis products or, a stated otherwise, 3-deazaadenosine and deazaadenosylhomocysteine have the ability to inhibit the enzyme adenosylhomocysteine hydrolase in the reaction mixture.

The effects of inhibition on the activity of S-adenosylhomocysteine hydrolase are as follows:

Table 1

Effects of S-Adenosyl-L-Homocysteine or Adenosine Analogs With Modifications in the Adenine Portions on Activity of S-Adenosyl-L-Homocysteine Hydrolase

| Compound | Inhibition at 1 mM % | $I_{50}$ mM | As Substrate in Exchange Reaction % Adenosylhomocysteine |
|---|---|---|---|
| S-3-Deazaadenosyl-L-homocysteine | 84 | 0.18 | 102 |
| 3-Deazaadenosine | 94 | 0.008 | — |

3-Deazaadenosine was found to be a powerful inhibitor of adenosylhomocysteine hydrolase. It has been observed that 3-deazaadenosine was not deaminated by the calf intestinal adenosine deaminase used. Thus, the hydrolysis of 3-deazaadenosylhomocysteine yields 3-deazaadenosine as one of the hydrolysis products. 3-Deazaadenosine had an $I_{50}$ of 8 $\mu$M, about 20 times smaller than that of 3-deazaadenosylhomocysteine. Therefore, the formation of 3-deazaadenosine by hydrolysis of less than 5% of 3-deazaadenosylhomocysteine at the $I_{50}$ concentration is sufficient to account for the inhibition observed.

In addition to the function or use of the compound 3-deazaadenosine in discouraging hydrolysis of the adenosylhomocysteine (AdoHcy), it has been found that the same compound has an active utility as an antiviral or antitumor (antifocal) agent and this has been verified in several tissue culture systems of animals. Use of tissue culture systems as screens for antitumor or antiviral activity of chemical agents is widespread and is as generally utilized as use of bacteria as screens for antibacterial agents. It is further noted that there is a different overall preferred range between the use of this compound as an inhibitor of the isolated enzyme adenosylhomocysteine hydrolase (0.001–0.008 mM, $I_{50}$) and the use of the same compound as an antiviral/antifocal agent (0.03–0.3 mM) in intact cells.

Table 2 below shows the antihydrolase property related to the use as an inhibitor of methylase and the antiviral activity and further shows that 3-deazaadenosine is superior to the 3-deazaadenosylhomocysteine in its effect on the AdoHcy hydrolase. Dosage of compounds utilized was at 0.1 mM.

TABLE 2

| | Inhibition of AdoHcy Hydrolase | Antiviral Activity |
|---|---|---|
| Adenosylhomocysteine (AdoHcy) | | |

TABLE 2-continued

| | Inhibition of AdoHcy Hydrolase | Antiviral Activity |
|---|---|---|
| naturally occurring inhibitor of methylases | — | — |
| Adenosylthioisobutyryl (SIBA) synthetic analog | + | + |
| 3-Deazaadenosylhomocysteine (3-Deaza-AdoHcy) | ++ | ++ |
| 3-Deazaadenosine | +++ + | ++ |
| Adenosine (hydrolysis product) | +++ + | — |

In separate experiments elevated levels of adenosylmethionine (AdoMet) and adenosylhomocysteine (AdoHcy) were observed in livers of rats injected with 3-deazaadenosine in the range 100–200 mg/kg of body weight and further it was found that 3-deazaadenosylhomocysteine was formed simultaneously. The increased level of adenosylhomocysteine as well as the formation of the synthetic 3-deaza-AdoHcy is shown in Example 1, post.

3-Deazaadenosine is an inhibitor of adenosylhomocysteine hydrolase as above and it affects the growth and development of virus in tissue culture systems, such as chick embryo cells and Rhesus monkey kidney culture. The inhibition of the development of viruses is similar to the inhibition of foci in tumor systems. The viral systems studied and observed were selected from the following: Rous sarcoma virus, influenza virus, vesicular stomatitis virus, Sindbis virus, and Newcastle disease virus. For example, in Rous sarcoma virus (RSV-BH) and its infectivity in chick embryo cells, there was a 500-fold reduction in the number of foci produced after administration of 0.1 mM 3-deazaadenosine to RSV-BH infected cells. Sensitivity to 3-deazaadenosine is maximal during the phase of virus replication that requires the synthesis of viral mRNA and protein and is minimal in the early stages of infection during which viral DNA is manufactured. Increased capacity for glucose uptake, a biochemical characteristic of chick embryo cells transformed by RSV-BH, is inhibited by 3-deazaadenosine. The ability of newly infected cells to grow in suspension is also inhibited by 3-deazaadenosine. After prolonged exposure to 3-deazaadenosine, the morphological phenotype characteristic of transformed cells largely disappeared, and the cells thus treated resembled noninfected cells. Exposure of Sindbis virus, Newcastle disease virus and vesicular stomatitis virus to 3-deazaadenosine resulted in a moderate reduction of cytolytic plaques formed. It has been found that 3-deazaadenosine in the 0.1 mM dosage had no effect on DNA or protein synthesis in cells and a slight effect on RNA synthesis and neither is it incorporated into cellular RNA. Incubation of chick embryo cells with 3-deazaadenosine results in an increase in the intracellular level of adenosylhomocysteine, with concomitant appearance of a relatively large amount of 3-deazaadenosylhomocysteine; the ratio of intracellular adenosylmethionine to adenosylhomocysteine, or (adenosylhomocysteine+3-deazaadenosylhomocysteine) is decreased from 150 to 19, and 1.4, respectively.

Thus, from the results obtained, it is noted that 3-deazaadenosine affects its inhibition of virus growth and replication by its ability to inhibit adenosylhomocysteine hydrolase although, as might be expected, concentration levels for viral inhibition (0.03–0.3 mM) in vivo are greater than inhibition of hydrolase (0.001–0.008 mM) in vitro.

The increase in the level of adenosylhomocysteine (AdoHcy) with the administration of 3-deazaadenosine and its antiviral effect is summarized in Examples 2–5, post. Further, with reference to Example 2 specially, it is apparent that with RSV-BH relative to the duration of treatment, the 3-deazaadenosine suppressed viral focus formation in the time period 24 hours to 7 days in a superior fashion and that this was better than the values for 0–24 hours after administration of the 3-deazaadenosine.

EXAMPLE 1

Table 3

Levels of adenosylmethionine (AdoMet), adenosylhomocysteine (AdoHcy), and 3-deazaadenosylhomocystein (3-deaza-AdoHcy) in rat livers after administration of 3-deazaadenosine.
3-Deazaadenosine, 20 mg/rat, was injected at 0 and 3 hours.

| | nanomoles/g liver | | | Ratios | |
|---|---|---|---|---|---|
| Hour | AdoMet | AdoHcy | 3-Deaza-AdoHcy | AdoMet/AdoHcy | AdoHcy + 3-Deaza-AdoHcy |
| 0 | 96 | 20 | 0 | 4.8 | 4.8 |
| 2 | 108 | 44 | 40 | 2.5 | 1.3 |
| 4 | 192 | 100 | 168 | 1.9 | 0.7 |
| 8 | 196 | 188 | 256 | 1.0 | 0.4 |
| 24 | 80 | 40 | 16 | 2.0 | 1.4 |

From the data above it would appear that the effectiveness of the administration of 3-deazaadenosine into the system is less than 24 hours and at a maximum of 8 hours (which is +8 from the first injection and +5 from the second injection).

In the above table the injection of 20 mg/rat was equivalent to the range 100–200 mg/kg of body weight.

EXAMPLE 2

3-Deazaadenosine was synthesized and supplied by Southern Research Institute, Birmingham, Ala.

Cells and Viruses:

Chick embryo cells were prepared from 10-day old embryos and replated at 2- and 3-day intervals. Cultures were grown in Eagle's Minimal Essential Medium (MEM) supplemented with dextrose (2 g/l final concentration), sodium pyruvate (5 mM), 10% hydrated tryptose phosphate broth (Difco), 5% fetal bovine serum, penicillin (50 U/ml), streptomycin (50 μg/ml) tylosin (50 μg/ml), and gentamycin (20 μg/ml). When effects of 3-deazaadenosine or other nucleosides were being tested, tryptose phosphate broth was eliminated from the medium. Cultures were maintained in humidified, $CO_2$—atmosphere incubators.

Sindbis virus, vesicular stomatitis virus, and Newcastle disease virus were propagated in chick embryo cells. For experiments with these viruses, cells were grown to confluency before infection. In examining virus reproduction, infected cultures were maintained on MEM containing 2% fetal bovine serum and antibiotics. Viruses were assayed by plaque-forming ability in chick embryo cells, using a nutrient agar overlay containing MEM, 2% fetal bovine serum, antibiotics, 1% agar, and 0.004% Neutral Red. Effects of 3-deazaadenosine were measured in the same medium.

Infection of sparsely distributed cells and development of infected cells into foci of transformed cells proceeded as described by J. Bader (1972) *Virology*, 48:485–493. Growth of cells suspended in nutrient agar also has been described by J. Bader (1967) *J. Cell. Physiol.*, 70:301–308.

Determination of intracellular levels of AdoMet, AdoHcy and 3-deaza-AdoHcy:

Levels of AdoMet, AdoHcy, and 3-deaza-AdoHcy were determined by high pressure liquid chromatography using VYDAC cation exchanger. Chick embryo cells were grown in a Petri dish for 7 days with 10 ml of [$^{35}$S]methionine (30.1 uCi) supplemented growth medium to achieve isototopic equilibrium. Each dish contained 10 million cells. After incubation with 3-deazaadenosine, the medium was poured off. Two ml of fresh MEM was added to each dish, and the cells were scraped off with a rubber policemen. Two dishes of cells were combined and homogenized with 0.4 ml of 50% sulfosalicylic acid in a ground glass homogenizer. The supernatant after centrifugation at 20,000×g for 10 min. was used for chromatographic analysis. The VYDAC cation column was calibrated with radioactive standards. The radioactive fractions, 1.2 ml each, were collected and radioactivity determined by using Aquasol (New England Nuclear) as scintillator. Standard 3-deaza-AdoHcy was synthesized by purified AdoHcy hydrolase.

RESULTS:

Inhibition of focus formation by 3-deazaadenosine.

The effects of 3-deazaadenosine on development of foci of virus transformed cells was examined. When a cell culture is exposed to an average of less than one infectious particle per cell, development of detectable morphological transformation requires 4 or 5 days. During this interval, the initially infected cell goes through several divisions, and many, if not all of the daughter cells, eventually change morphology, appearing as a focus of transformed cells against a background of nontransformed cells. Transformation induced by RNA tumor viruses is divided into two easily distinguishable phases: (1) events prior to and including the synthesis of viral DNA and (2) events following and no longer requiring the synthesis of viral DNA. Synthesis of the DNA of RSV-BH begins within the first hour after infection and is required for no more than 8 hours.

The effects of 3-deazaadenosine on focus formation depends on the time of its addition to chick embryo cells after infection. Addition of 3-deazaadenosine during the first 8 hours after infection; i.e., during the time critical to DNA synthesis, had no effect on subsequent transformation. Addition of 3-deazaadenosine to the culture medium for longer time intervals (24 hours) immediately following infection resulted in a moderate reduction in the number of foci observable after 7 days. A striking inhibition of focus formation was observed if 3-deazaadenosine was added 24 hours after infection and left in the culture for the duration of the week (Table 4). The effective concentration, 0.1 mM, was not toxic to the cells as evidenced by their normal growth over the next 7 days.

TABLE 4

Effect of 3-deazaadenosine on focus formation induced by RSV-BH[a]

| Treatment | Viral Focus Formation Duration of Treatment | |
|---|---|---|
| | 0 to 24 h | 24 h to 7 days |
| None | 1.0 | 1.0 |
| 3-Deazaadenosine | | |
| 0.3 mM | 0.01 | .001 |
| 0.1 mM | 0.21 | .002 |
| 0.03 mM | — | .31 |

[a]Cells were exposed to RSV-BH for 30 min., then growth medium or the same medium containing 3-deazaadenosine was added. 24 h later medium was removed and nutrient Focus Agar was added. Some previously untreated cultures received Focus Agar containing the adenosine analogs.

EXAMPLE 3

TABLE 5

Effect of 3-deazaadenosine on cytolytic RNA viruses.[a]

| Virus | 3-Deazaadenosine (mM) | | | |
|---|---|---|---|---|
| | 0 | 0.03 | 0.1 | 0.3 |
| | Plaques/Culture | | | |
| Vesicular stomatitis | 54[b] | 44 | 39[c] | 22[d] |
| Sindbis | 60 | 60 | 52[c] | 36[d] |
| Newcastle disease | 125 | 112 | 83[c] | 71[d] |

[a]Confluent chick embryo cells were treated with 3-deazaadenosine for 18 h before exposure to vesicular stomatitis virus, Sindbis virus, or Newcastle disease virus. Cytolytic plaques were counted 2 days later.
[b]Plaques per culture, average of 2 plates.
[c]These plaques were smaller than those in non-treated cultures.
[d]Minute plaques.

EXAMPLE 4

TABLE 6

Effect of 3-deazaadenosine on reproduction of vesicular stomatitis virus.[a]

| Treatment | PFU × 10$^6$/culture |
|---|---|
| None | 430 |
| 3-Deazaadenosine (0.1 mM) | |
| Pretreated 18 h | 21 |
| Treated after infection | 110 |

[a]Vesicular stomatitis virus was added at high multiplicity (about 10 PFU per cell). Fluids were collected 9 h after infection and assayed for plaque forming ability. PFU = plaque forming units.

EXAMPLE 5

TABLE 7

24-Hour yield of A/Vic/3/75 (H3N2) wild type influenza virus grown in Rhesus monkey kidney culture

| Experiment No. | Concentration of Drug | Titer of Virus (log$_{10}$TCID$_{50}$/ml) | Reduction (log$_{10}$) |
|---|---|---|---|
| 1 | 0 μM | 6.25 | — |
| | 10 μM | 6.50 | −.25 |
| | 25 μM | 6.00 | .25 |
| | 50 μM | 5.75 | .50 |
| | 75 μM | 5.50 | .75 |
| | 100 μM | 5.00 | 1.25 |
| 2 | 0 μM | 6.75 | — |
| | 10 μM | 7.25 | −.50 |
| | 100 μM | 6.25 | .50 |
| | 250 μM | 5.00 | 1.75 |
| | 500 μM | 5.00 | 1.75 |
| | 1000 μM | 5.50 | 1.25 |

These data indicated that at concentrations of 3-deazaadenosine of 100–1000 μM there was a 30 to 90-fold reduction in virus yield at 24 hours.

We claim:

1. A method of producing an antiviral effect in a tissue culture system comprising applying to said tissue culture system an effective antiviral amount of 3-deazaadenosine.

2. The method according to claim 1 wherein the antiviral amount utilized is in the range of 0.03–0.3 mM.

3. The method according to claim 1 wherein 3-deazaadenosine is utilized in a tissue culture system of chick embryo cells mixed with Rous sarcoma virus (RSV-BH).

4. The method according to claim 1 wherein 3-deazaadenosine is utilized in a tissue culture system wherein the chick embryo is mixed with a cytolytic RNA virus selected from a member of the group consisting of vesicular stomatitis virus, Sindbis virus, and Newcastle disease virus to inhibit virus focal formation.

5. The method according to claim 1 wherein 3-deazaadenosine is utilized in a tissue culture system of Rhesus monkey kidney culture mixed with A/Vic/3/75 (H3N2) wild type influenza virus and the virus focal formation is inhibited.

6. A method of inhibiting adenosylhomocysteine hydrolase comprising administering to a rat an effective amount of from 100–200 mg/kg of body weight of 3-deazaadenosine to inhibit said adenosylhomocysteine hydrolase.

7. An enzyme inhibitor system consisting essentially of adenosylhomocysteine hydrolase of beef liver and 3-deazaadenosine as an active ingredient in effective amounts of from 0.001 to 0.008 mM($I_{50}$) as an inhibitor of said adenosylhomocysteine hydrolase.

* * * * *